United States Patent
Sato et al.

(10) Patent No.: US 8,163,857 B2
(45) Date of Patent: Apr. 24, 2012

(54) POLYFLUOROALKADIENE MIXTURE AND METHOD FOR PRODUCING THE SAME

(75) Inventors: Katsuyuki Sato, Ibaraki (JP); Seiichiro Murata, Ibaraki (JP); Akihiko Ikeda, Ibaraki (JP); Daisuke Murai, Ibaraki (JP); Mitsuru Maeda, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 12/993,571

(22) PCT Filed: Jun. 12, 2009

(86) PCT No.: PCT/JP2009/060731
§ 371 (c)(1),
(2), (4) Date: Nov. 19, 2010

(87) PCT Pub. No.: WO2009/151109
PCT Pub. Date: Dec. 17, 2009

(65) Prior Publication Data
US 2011/0077371 A1 Mar. 31, 2011

(30) Foreign Application Priority Data
Jun. 13, 2008 (JP) ................ 2008-154915

(51) Int. Cl.
*C07C 21/19* (2006.01)
*C07C 17/25* (2006.01)
*C08F 214/18* (2006.01)
*C08F 236/20* (2006.01)

(52) U.S. Cl. ............... 526/250; 526/252; 526/253

(58) Field of Classification Search ............ 526/250, 526/252, 253
See application file for complete search history.

(56) References Cited

U.S. PATENT DOCUMENTS
4,035,565 A 7/1977 Apotheker et al.

FOREIGN PATENT DOCUMENTS

| JP | 54-1585 | 1/1979 |
|---|---|---|
| JP | 59-108081 | 6/1984 |
| JP | 63-308008 | 12/1988 |
| JP | 10-130341 | 5/1998 |
| JP | 2003-221406 | 8/2003 |
| JP | 2003-246757 | 9/2003 |

OTHER PUBLICATIONS

International Search Report from corresponding PCT application No. PCT/JP2009/060731 dated Sep. 15, 2009, 2 pgs.
International Preliminary Report on Patentability and Written Opinion from corresponding PCT application No. PCT/JP2009/060731 dated Jan. 20, 2011, 5 pages.

*Primary Examiner* — Nathan M Nutter
(74) *Attorney, Agent, or Firm* — Brinks Hofer Gilson & Lione

(57) ABSTRACT

A mixture of polyfluoroalkadienes represented by the general formulae: $CF_3(CF_2)_nCF=CH(CF_2)_{m+1}CH=CH_2$ [Ia] and $CF_3(CF_2)_{n+1}CH=CF(CF_2)_mCH=CH_2$ [Ib], wherein n is an integer of 0 to 5, and m is an integer of 0 to 6, is obtained as a mixture fraction of products [Ia] and [Ib] by reacting a polyfluoroalkyl iodide represented by the general formula: $CF_3(CF_2)_{n+1}CH_2(CF_2)_{m+1}(CH_2CH_2)I$ [II], with an organic basic compound. The polyfluoroalkadiene mixture is compounds having a perfluoroalkyl group in which the number of successive $CF_2$ groups is 5 or less, and is effectively used as a copolymerizable monomer in the production of resinous or elastomeric fluorine-containing copolymers, which are used as active ingredients of surface-treating agents, such as water- and oil-repellents and mold-release agents.

12 Claims, No Drawings

POLYFLUOROALKADIENE MIXTURE AND METHOD FOR PRODUCING THE SAME

RELATED APPLICATION

This application is a 35 U.S.C. §371 national phase filing of International Patent Application No. PCT/JP2009/060731, filed Jun. 12, 2009, through which and to which priority is claimed under 35 U.S.C. §119 to Japanese Patent Application No. 2008-154915, filed Jun. 13, 2008.

TECHNICAL FIELD

The present invention relates to a polyfluoroalkadiene mixture and a method for producing the same. More specifically, the present invention relates to a polyfluoroalkadiene mixture that is compounds having a perfluoroalkyl group containing 6 or less carbon atoms and that is used as a copolymerizable monomer in the production of fluorine-containing copolymers serving as active ingredients of, for example, water- and oil-repellents; and a method for producing the polyfluoroalkadiene mixture.

BACKGROUND ART

Acrylic acid derivatives of perfluoroalkyl alcohols (e.g., $CF_3(CF_2)_7CH_2CH_2OCOCH=CH_2$) are used in large amounts as monomers for synthesizing water- and oil-repellents for textile. Moreover, perfluoroalkyl alcohols serving as starting materials of the acrylates are widely used as, for example, surfactants (see Patent Document 1).

Such compounds having a perfluoroalkyl group as a structural unit are generally known to be able to improve surface modification properties, water- and oil-repellency, antifouling properties, mold-release properties, leveling properties, and other properties, when applied on the surfaces of fiber, metal, glass, rubber, resin, etc. Particularly, compounds having a $C_8$-$C_{12}$ perfluoroalkyl group (telomer compounds) are most likely to develop the aforementioned desired performance, and therefore, $C_8$ telomer compounds are particularly preferably used.

On the other hand, it is reported that in particular, telomer compounds having a $C_8$-$C_{12}$ perfluoroalkyl group are biologically degraded in the environment and converted to compounds having relatively high bioaccumulative and environmental concentration, causing concerns for exposure during treatment processes, and release or diffusion from waste, treated substrates, etc., into the environment. Moreover, compounds having a perfluoroalkyl group containing 14 or more carbon atoms are very difficult to handle because of their physicochemical properties, and hence, such compounds are rarely used in practice.

As for telomer compounds having a perfluoroalkyl group containing 8 or more carbon atoms, generation and incorporation of perfluorooctanoic acids with high bioaccumulation potential is unavoidable during the production of the telomer compounds.

For these reasons, companies that produce such telomer compounds have retreated from the production of the compounds or promoted the use of alternative compounds having a perfluoroalkyl group containing 6 or less carbon atoms. However, compounds having a perfluoroalkyl group containing 6 or less carbon atoms cause a significant decrease in orientation on the surface of a treated substrate, and the melting point, glass transition point, etc., of the compounds are markedly lower than those of $C_8$ compounds. Accordingly, the compounds are highly influenced by their using environ-mental conditions, such as temperature, humidity, stress, and the organic solvent, and the desired performance cannot be sufficiently achieved. In addition, durability and other properties are affected.

PRIOR ART DOCUMENT

Patent Document

Patent Document 1: JP-B-63-22237
Patent Document 2: JP-A-10-130341
Patent Document 3: JP-A-63-308008
Patent Document 4: JP-B-58-4728
Patent Document 5: JP-B-54-1585

OUTLINE OF THE INVENTION

Problem to be Solved by the Invention

An object of the present invention is to provide a polyfluoroalkadiene mixture that is compounds having a perfluoroalkyl group in which the number of successive $CF_2$ groups is 5 or less, and that is effectively used as a copolymerizable monomer in the production of resinous or elastomeric fluorine-containing copolymers, which are used as active ingredients of surface-treating agents, such as water- and oil-repellents and mold-release agents; and to provide a method for producing the polyfluoroalkadiene mixture.

Means for Solving the Problem

The present invention provides a mixture of polyfluoroalkadienes represented by the general formulae:

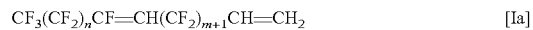
$$CF_3(CF_2)_nCF=CH(CF_2)_{m+1}CH=CH_2 \quad \text{[Ia]}$$

and

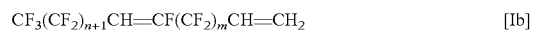
$$CF_3(CF_2)_{n+1}CH=CF(CF_2)_mCH=CH_2 \quad \text{[Ib]}$$

wherein n is an integer of 0 to 5, and m is an integer of 0 to 6. The polyfluoroalkadiene mixture is produced as a mixture fraction of products [Ia] and [Ib] by reacting a polyfluoroalkyl iodide represented by the general formula:

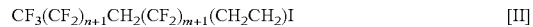
$$CF_3(CF_2)_{n+1}CH_2(CF_2)_{m+1}(CH_2CH_2)I \quad \text{[II]}$$

wherein n is an integer of 0 to 5, and m is an integer of 0 to 6, with an organic basic compound.

EFFECT OF THE INVENTION

The polyfluoroalkadiene mixture of the present invention has an unsaturated structure that is vulnerable to ozone decomposition, when released into the environment, and can be easily decomposed into compounds with low environmental concentration and low bioaccumulation potential. Moreover, the polyfluoroalkadiene mixture does not produce environmental loading substances, such as perfluoroalkyl carboxylic acids, in the production process thereof.

Such an environmentally superior polyfluoroalkadiene mixture of the present invention can effectively be used as a copolymerizable monomer for the production of fluorine-containing copolymers that can improve performance such as surface modification properties, water- and oil-repellency, antifouling properties, mold-release properties, and leveling properties, which cannot be achieved or can be achieved only insufficiently by telomers having 6 or less carbon atoms, compared with $C_8$ telomers.

Furthermore, a fluorine-containing copolymer obtained by copolymerizing the polyfluoroalkadiene mixture with a fluorinated olefin monomer can be used as a fluorine-containing elastomer for peroxide crosslinking.

MODES FOR CARRYING OUT THE INVENTION

The polyfluoroalkadiene mixture of the present invention is produced as a mixture of products [Ia] and [Ib] by reacting a polyfluoroalkyl iodide represented by the general formula:

$$CF_3(CF_2)_nCH_2(CF_2)_{m+1}(CH_2CH_2)I \qquad [II]$$

n: 0 to 5
m: 0 to 6 with an organic basic compound to carry out an HI-elimination reaction, while the —$CF_2CH_2CF_2$— bond is subjected to an HF-elimination reaction.

Here, the mixture of products [Ia] and [Ib] is formed because in the HF-elimination reaction that is carried out together with the HI-elimination reaction, the elimination of the H atom of the methylene chain $CH_2$ and the F atom of either one of the fluoromethylene chains $CF_3$ linking back and forth to the H atom occurs equally in the anteroposterior position. Moreover, since the HF-elimination reactions of the produced polyfluoroalkadiene mixtures are equivalent, the proportion of the produced products [Ia] and [Ib] is approximately 1:1. Although the products [Ia] and [Ib] cannot be separately identified because they are very similar constitutional isomers, a mixture of these compounds can be directly sued as a synthetic starting material or other substances because they have equivalent reactivity.

For example, when polyfluoroalkyl iodides, in which n is 3, and m+1 is 5 or 3, is used as a starting material, these compounds can be obtained by the method shown in the Reference Examples described later.

The polyfluoroalkyl iodide can also be obtained by the addition reaction of terminally iodized polyfluoroalkane with ethylene. Examples of terminally iodized polyfluoroalkane include compounds of the following formulae:

$$CF_3(CF_2)(CH_2CF_2)I$$

$$CF_3(CF_2)_2(CH_2CF_2)I$$

$$CF_3(CF_2)_3(CH_2CF_2)I$$

$$CF_3(CF_2)_4(CH_2CF_2)I$$

$$CF_3(CF_2)(CH_2CF_2)(CF_2CF_2)I$$

$$CF_3(CF_2)(CH_2CF_2)(CF_2CF_2)_2I$$

$$CF_3(CF_2)_2(CH_2CF_2)(CF_2CF_2)I$$

$$CF_3(CF_2)_2(CH_2CF_2)(CF_2CF_2)_2I$$

The polyfluoroalkyl iodide of the general formula:

$$CF_3(CF_2)_{n+1}CH_2(CF_2)_{m+1}(CH_2CH_2)I \qquad [II]$$

i.e., the general formula:

$$CH_3(CF_2)_{n+1}(CH_2CF_2)(CF_2CF_2)_p(CH_2CH_2)I \qquad (m=2p)$$

can be produced by the addition reaction of a terminally iodized compound represented by the general formula:

$$CF_3(CF_2)_{n+1}(CH_2CF_2)(CF_2CF_2)_pI \qquad [A],$$

with ethylene.

The ethylene addition reaction is carried out in such a manner that the above compound [A] is subjected to an addition reaction with pressurized ethylene in the presence of a peroxide initiator. The number of addition is 1 or more, and preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or below. As a peroxide initiator, tert-butyl peroxide, di(tert-butylcyclohexyl)peroxy dicarbonate, dicetyl-peroxy dicarbonate, or the like may be used at a ratio of about 1 to 5 mol % based on the amount of compound [A].

The polyfluoroalkane iodide [II] is reacted with an organic basic compound to carry out dehydrohalogenation reaction, thereby resulting in an HI-elimination reaction at position 1 and an HF-elimination reaction between the $CH_2$ group on the side of the perfluoroalkyl group and either of $CF_2$ groups adjacent thereto. Thus, a mixture of polyfluoroalkadienes [Ia] and [Ib] is produced.

Examples of organic basic compounds include diethylamine, triethylamine, pyridine or a derivative thereof, diethanolamine, triethanolamine, 1,8-diazabicyclo[5.4.0]-7-undecene, diazabicyclononene, and other nitrogen-containing organic basic compounds; and sodium methoxide, sodium ethoxide, potassium methoxide, and other alkoxides of monovalent metals. Preferably, nitrogen-containing organic basic compounds having low nucleophilicity are used, and 1,8-diazabicyclo[5.4.0]-7-undecene is particularly preferably used.

Such an organic basic compound is used in a molar ratio of about 0.1 to 10, preferably 0.95 to 3.5, and more preferably 1.95 to 2.5, with respect to the polyfluoroalkane iodide [II]. When 1,8-diazabicyclo[5.4.0]-7-undecene is used in a fluorine-containing organic solvent, or triethylamine is used in a tetrahydrofuran solvent, in a more preferable molar ratio of 1.95 to 2.5, a mixture of polyfluoroalkadienes [Ia] and [Ib] is mainly produced in a yield of about 75%. In other cases, a compound of the formula: $C_4F_9CH_2(CF_2)_4CH=CH_2$, and other compounds are produced as by-products, in addition to the products [Ia] and [Ib]; however, such by-products can be separated by fractional distillation. When the amount of organic basic compound is less than this range, the desired dehydrohalogenation reaction does not proceed smoothly; whereas when the amount is more than this range, the removal of the organic basic compound becomes difficult, and side reactions is caused, resulting in an increased amount of waste.

Although the dehydrohalogenation reaction can be carried out in the absence of a solvent, the reaction is preferably carried out in the presence of water or an organic solvent in terms of reaction efficiency and control of heating generation. Examples of organic solvents include alcohols, such as methanol, ethanol, propanol, and isopropanol; ethers, such as diethyl ether, 1,4-dioxane, and tetrahydrofuran; ketones, such as acetone, methyl ethyl ketone, and methyl isobutyl ketone; aromatic or alicyclic hydrocarbons, such as toluene and cyclohexane; aprotic polar solvents, such as acetonitrile, N,N-dimethylformamide, N,N-diethylformamide, N,N-dimethylacetamide, N,N-diethylacetamide, and N-methyl-2-pyrrolidone; and fluorine-containing organic solvents, such as hydrochlorofluorocarbon (e.g., HCFC-225) and hydrofluoroether (e.g., Novec HFE; a product of 3M).

Water or an organic solvent is used in a volume ratio of about 0.1 to 100, preferably about 1 to 10, and more preferably 3 to 6, with respect to the polyfluoroalkane iodide [II]. However, a larger amount of solvent does not affect the reaction efficiency, and thus the solvent is preferably used in a volume ratio of 3 to 6.

The dehydrohalogenation reaction is carried out at about −20 to 100° C., and preferably about −10 to 80° C. Side reactions proceed at temperatures higher than this range, generating a large amount of by-products with an unknown structure. The reaction may be carried out at reduced pressure, atmospheric pressure, or increased pressure; in terms of ease of handling the reaction apparatus, the reaction is preferably carried out under atmospheric pressure.

In a case of static phase separation is performed after the reaction is completed, the separated organic layer is washed with water, for example, to remove the organic basic compound, and purification is then performed by distillation etc., according to a standard method, thereby obtaining the target polyfluoroalkadiene mixture. For example, in a case of a polar solvent is used instead of performing static phase separation, the solvent is distilled off under reduced pressure, followed by the same treatment as in the case where static phase separation is carried out.

The polyfluoroalkadiene mixture obtained in this manner is copolymerized with, for example, a fluorinated olefin monomer represented by the general formula: $CX_2=CXY$ to form a fluorine-containing elastomer. Here, X is H or F, and Y is H, F, $C_nF_{2n+1}$ (n: 1 to 3), or $O[CF(Z)CF_2O]_m C_nF_{2n+1}$ (Z: F or $CF_3$, n: 1 to 3, and m: 0 to 5). X and Y are the same or different, and at least one of X and Y is a fluorine atom or a fluorine-containing group.

The fluorinated olefin monomer represented by the above general formula to be copolymerized with the polyfluoroalkadiene mixture is, for example, at least one of vinylidene fluoride, tetrafluoroethylene, hexafluoropropylene, perfluoro (lower alkyl vinyl ether) having a lower alkyl group containing 1 to 3 carbon atoms, perfluoro vinyl ether represented by the general formula: $CF_2=CFO[CF(CF_3)CF_2O]_n CF_3$ (n: 1 to 5), and the like. More specifically, vinylidene fluoride-tetrafluoroethylene copolymers, vinylidene fluoride-tetrafluoroethylene-hexafluoropropylene copolymers, vinylidene fluoride-tetrafluoroethylene-perfluoro(lower alkyl vinyl ether), and other vinylidene fluoride-tetrafluoroethylene-based copolymers can be used as preferred fluorine-containing elastomers.

The polyfluoroalkadiene mixture, which is to be copolymerized in the fluorine-containing elastomer in an amount of about 1.5 mol % or less, and preferably about 0.02 to 0.5 mol % (about 5 wt. % or less, and preferably about 0.1 to 2 wt. %, based on the total amount of charged monomer), is a bifunctional monomer having two kinds of unsaturated bonds having different reactivities with each other. The polyfluoroalkadiene mixture can produce a fluorine-containing elastomer cross-linked product having more excellent vulcanizate physical properties and compression set characteristics, compared with a fluorine-containing elastomer which no polyfluoroalkadiene is copolymerized, or a fluorine-containing elastomer which another bifunctional monomer represented by the general formula: $CF_2=CF[OCF_2CF(CF_3)]_m OCF_2CF_2O[CF(CF_3)CF_2O]_n CF=CF_2$ (m+n is an integer of 0 to 8) is copolymerized in place of polyfluoroalkadienes.

It is conventionally known that the copolymerization of a polyfunctional unsaturated monomer in a fluorine-containing elastomer results in an improvement in compression set characteristics of cross-linked products; however, while this property is improved, there is a problem that the vulcanizate physical properties (particularly elongation at break characteristics) of cross-linked products are inevitably lowered. This problem may possibly be improved by changing the structure between the unsaturated functional groups of the polyfunctional unsaturated monomer (control of the chain length); however, compression set characteristics and vulcanizate physical properties (particularly elongation characteristics) have a trade-off relationship with each other, and both characteristics cannot be satisfied simultaneously. The copolymerization of polyfluoroalkadienes of the present invention can produce a fluorine-containing elastomer that satisfies both characteristics.

Together with the polyfluoroalkadiene mixture, a bromine or iodine group-containing unsaturated monomer compound, preferably a bromine group-containing unsaturated monomer compound, can be copolymerized in an amount of about 5 mol % or less, and preferably about 1 mol %, in the fluoroelastomer. Thereby, the crosslinking characteristics of the obtained fluoroelastomer (e.g., elongation at break, strength at break, and compression set characteristics) can be further improved.

Examples of bromine group-containing unsaturated monomer compounds include vinyl bromide, 2-bromo-1,1-difluoroethylene, perfluoroallyl bromide, 4-bromo-1,1,2-trifluorobutene-1, 4-bromo-3,3,4,4-tetrafluorobutene-1, 4-bromo-1,1,3,3,4,4-hexafluorobutene-1, bromotrifluoroethylene, 4-bromo-3-chloro-1,1,3,4,4-pentafluorobutene-1, 6-bromo-5,5,6,6-tetrafluorohexene-1, 4-bromoperfluorobutene-1, 3,3-difluoroallyl bromide, and other brominated vinyl compounds or brominated olefins; preferably, a bromine-containing vinyl ether represented by the following general formula is used:

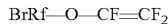

$BrRf$—O—$CF=CF_2$

BrRf: a bromine group-containing perfluoroalkyl group
Examples of such bromine group-containing vinyl ethers include those represented by the following formulae: $BrCF_2CF_2OCF=CF_2$, $BrCF_2(CF_2)_2OCF=CF_2$, $BrCF_2(CF_2)_3OCF=CF_2$, $CF_3CFBr(CF_2)_2OCF=CF_2$, and $BrCF_2(CF_2)_4OCF=CF_2$.

Moreover, examples of usable iodine-containing unsaturated monomer compounds include iodotrifluoroethylene, 1,1-difluoro-2-iodoethylene, perfluoro(2-iodoethyl vinyl ether), iodinated vinyl, and the like.

In place of or together with these bromine or iodine group-containing unsaturated monomer compounds, a bromine- and/or iodine-containing compound represented by the general formula: $R(Br)_n(I)_m$, wherein R is a $C_2$-$C_6$ saturated fluorohydrocarbon group or a saturated chlorofluorohydrocarbon group, n and m are 0, 1 or 2, and m+n is 2, can be used, and the copolymerization reaction of polyfluoroalkadienes and other fluorinated olefin monomers can be carried out in the presence of such a compound. These bromine- and/or iodine-containing compounds are well-known, as described in, for example, Patent Documents 2 to 5.

Furthermore, when these compounds are used, they act as chain transfer agents and function to control the molecular weight of the produced fluorine-containing copolymer. Additionally, the chain transfer reaction produces a fluorine-containing copolymer in which bromine and/or iodine are bound to the molecular ends, and these sites form crosslinking sites. More specifically, when a known iodide represented by the general formula: $IC_nF_{2n}I$ (e.g., $I(CF_2)_4I$), and a halide represented by the general formula: $IC_nF_{2n}Br$ (e.g., $IC(CF_2)_4Br$ or $I(CF_2)_2Br$) are used in combination as chain transfer agents, there is another advantage that a halogen atom, which is bound to the molecular end and is radically activity, can be used as a crosslinking point at which peroxide crosslinking can occur.

The copolymerization reaction is carried out by an aqueous emulsion polymerization method or an aqueous suspension polymerization method. In the aqueous emulsion polymerization method, a water-soluble peroxide alone or a redox system prepared by combining a water-soluble peroxide with a water-soluble reducing substance can be used as a reaction initiator system. Examples of the water-soluble peroxide include ammonium persulfate, potassium persulfate, sodium persulfate, and the like. Examples of the water-soluble reducing substance include sodium sulfite, sodium hydrogen sulfite, and the like. In this case, pH regulators (buffers), such as sodium monohydrogen phosphate, sodium dihydrogen phosphate, potassium monohydrogen phosphate, and potassium dihydrogen phosphate, can be used as stabilizers in the produced aqueous emulsion.

The emulsion polymerization reaction is carried out in the presence of an emulsifier represented by the general formula:

RfCOOM

Rf: a fluoroalkyl group, a perfluoroalkyl group, a fluoroxyalkyl group, a perfluorooxyalkyl group, or the like M: an ammonium salt or an alkali metal The amount of emulsifier used is about 0.1 to 20 wt. %, and preferably about 0.2 to 2 wt. %, based on the amount of water.

Examples of the emulsifer represented by the above formula include those represented by the following formulae:

$C_5F_{11}COONH_4$ $C_5F_{11}COONa$ $C_6F_{13}COONH_4$ $C_6F_{13}COONa$ $C_6HF_{12}COONH_4$ $C_6HF_{12}COONa$ $C_6H_2F_{11}COONH_4$ $C_6H_2F_{11}COONa$ $C_7F_{15}COONH_4$ $C_7F_{15}COONa$ $C_7HF_{14}COONH_4$ $C_7HF_{14}COONa$ $C_7H_2F_{13}COONH_4$ $C_7H_2F_{13}COONa$ $C_8F_{17}COONH_4$ $C_8F_{17}COONa$ $C_8HF_{16}COONH_4$ $C_8HF_{16}COONa$ $C_8H_2F_{15}COONH_4$ $C_8H_2F_{15}COONa$ $C_9F_{19}COONH_4$ $C_9F_{19}COONa$ $C_9HF_{18}COONH_4$ $C_9HF_{18}COONa$ $C_9H_2F_{17}COONH_4$ $C_9H_2F_{17}COONa$ $C_3F_7OCF(CF_3)COONH_4$ $C_3F_7OCF(CF_3)COONa$ $C_3F_7OCF(CF_3)CF_2OCF(CF_3)COONH_4$ $C_3F_7OCF(CF_3)CF_2OCF(CF_3)COONa$ $C_3F_7O[CF(CF_3)CF_2O]_2CF(CF_3)COONH_4$ $C_3F_7O[CF(CF_3)CF_2O]_2CF(CF_3)COONa$ $C_3F_7O[CF(CF_3)CF_2O]_3CF(CF_3)COONH_4$ $C_3F_7O[CF(CF_3)CF_2O]_3CF(CF_3)COONa$

The molecular weight can be controlled by adjusting the relationship between the copolymerization rate and the amount of initiator. Alternatively, the control of molecular weight can also be easily performed by using chain transfer agents, such as $C_4$-$C_6$ hydrocarbons, alcohols, ethers, esters, ketones, and organic halides.

The reaction temperature and reaction pressure vary depending on the degradation temperature of the initiator used and the copolymer composition of the desired copolymer. In order to obtain an elastomeric copolymer, the reaction is generally carried out at about 0 to 100° C., and preferably about 40 to 80° C., at about 0.8 to 4.5 MPa·G, and preferably about 0.8 to 4.2 MPa·G.

The fluorine-containing elastomer obtained in this manner has iodine etc. that are derived from a fluoroolefin iodide and that act as peroxide crosslinkable groups in the copolymer. Therefore, the elastomer can be subjected to peroxide crosslinking with an organic peroxide. Examples of the organic peroxide to be used for peroxide crosslinking include 2,5-dimethyl-2,5-bis(tert-butylperoxy)hexane, 2,5-dimethyl-2,5-bis(tert-butylperoxy)hexyne-3, benzoyl peroxide, bis(2,4-dichlorobenzoyl) peroxide, dicumyl peroxide, di-tert-butyl peroxide, tert-butyl cumyl peroxide, tert-butylperoxybenzene, 1,1-bis(tert-butylperoxy)-3,5,5-trimethylcyclohexane, 2,5-dimethylhexane-2,5-dihydroxyperoxide, α,α'-bis(tert-butylperoxy)-p-diisopropylbenzene, 2,5-dimethyl-2,5-di(benzoylperoxy)hexane, tert-butylperoxy isopropyl carbonate, and the like.

In the peroxide crosslinking method using these organic peroxides, polyfunctional unsaturated compounds, such as tri(meth)allyl isocyanurate, tri(meth)allyl cyanurate, triallyl trimellitate, N,N'-m-phenylene bismaleimide, diallyl phthalate, tris(diallylamine)-s-triazine, triallyl phosphite, 1,2-polybutadiene, ethylene-glycol diacrylate, diethylene glycol diacrylate, and the like are generally used as co-crosslinking agents in combination with the organic peroxides for the purpose of obtaining more excellent vulcanizate physical properties, mechanical strength, compression set characteristics, etc.

Further, depending on the purpose, oxides or hydroxides of divalent metals (e.g., oxides or hydroxides of calcium, magnesium, lead, zinc, and the like) can also be used as crosslinking aids. These compounds act also as acid acceptors.

The proportion of each component compounded with the peroxide crosslinking system is generally as follows (based on 100 parts by weight of fluorine-containing elastomer):

Organic peroxide: about 0.1 to 10 parts by weight, and preferably about 0.5 to 5 parts by weight Co-crosslinking agent: about 0.1 to 10 parts by weight, preferably about 0.5 to 5 parts by weight Crosslinking aid: about 15 parts by weight or less Thus, a fluorine-containing elastomer composition is formed. In addition to the above components, conventionally known fillers, reinforcing agents, plasticizers, lubricants, processing aids, pigments, and the like may suitably be compounded into the composition.

Peroxide crosslinking is carried out by mixing the above components using a generally used mixing method, such as roll mixing, kneader mixing, Banbury mixing, and solution mixing, followed by heating. Heating is generally carried out by press vulcanization performed at about 100 to 250° C. for about 1 to 120 minutes, and oven vulcanization (secondary vulcanization) performed at about 150 to 300° C. for about 0 to 30 hours.

EXAMPLES

The following describes the present invention with reference to Examples.

Reference Example 1

A compound of the formula: $CF_3(CF_2)_3(CH_2CF_2)(CF_2CF_2)_2I$ (99 GC %) (603 g; 0.99 mol) and 7 g (0.05 mol) of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 41 g (1.45 mol) of ethylene was introduced over about 3 hours. The content was collected at an internal temperature of 50° C. or less, thereby obtaining 637 g (yield: 98.8%) of a compound of the formula: $CF_3(CF_2)_3(CH_2CF_2)(CF_2CF_2)_2(CH_2CH_2)I$ (98 GC %), i.e., the formula: $C_4F_9CH_2(CF_2)_5CH_2CH_2I$.

Example 1

3,3,4,4,5,5,6,6,7,7,9,9,10,10,11,11,12,12,12-nonadecafluoro-1-iodododecane of the formula: $C_4F_9CH_2(CF_2)_5CH_2CH_2I$ (5 g; 7.8 mmol) obtained in above Reference Example 1 was dissolved in 15 ml of fluorine-containing organic solvent (AK-225; a product of Asahi Glass), and the resulting solution was placed in a 50-ml glass reactor equipped with a cooling condenser, thermocouple, and magnet stirrer. After ice cooling, 2.6 g (17.2 mmol) of 1,8-diazabicyclo[5.4.0]-7-undecene [DBU] was added dropwise, while maintaining the internal temperature in a range of 0 to 10° C. After completion of the addition, the mixture was stirred at about 0° C. for about 1 hour, and stirring was then continued at room temperature for about 23 hours (total reaction time: 24 hours).

After the reaction was completed, washing with 20 ml of water was performed twice, and subsequently washing with a saturated saline solution was performed once. The obtained reaction product solution was dehydrated and dried over anhydrous magnesium sulfate. After the reaction solvent was distilled off under reduced pressure, the residue was purified by distillation under reduced pressure, thereby obtaining 2.8 g (yield: 77%) of a fraction with a vapor temperature of 68 to 70° C./1 kPa. The structure of the obtained fraction was determined by $^{19}F$-NMR and $^{1}H$-NMR, and the fraction was identified as a mixture of products A and B having a weight ratio of about 48:52.

Product A: 3,3,4,4,5,5,6,6,7,7,9,10,10,11,11,12,12,12-octadecafluorododeca-1,8-diene
$CF_3CF_2CF_2CF=CHCF_2CF_2CF_2CF_2CH=CH_2$
Product B: 3,3,4,4,5,5,6,6,7,9,9,10,10,11,11,12,12,12-octadecafluorododeca-1,7-diene
$CF_3CF_2CF_2CF_2CH=CFCF_2CF_2CF_2CH=CH_2$
$^{1}H$-NMR: TMS
Product A δ=5.81 (1H:—CF=CH—), 5.79 (1H:—CF$_2$—CH=), 5.97 (2H:=CH$_2$)
Product B δ=5.81 (1H:—CH=CF—), 5.79 (1H:—CF$_2$—CH=), 5.97 (2H:=CH$_2$)
$^{19}F$-NMR: CFCl$_3$
Product A δ=−79.95 (3F:CF$_3$—), −108.35 (2F:=CHCF$_2$—), −111.34(1F:-CF=), −112.34 (2F:—CF$_2$CH=), −117.4 to 126.3 (10F:-CF$_2$—)
Product B δ=−80.20 (3F:CF$_3$—), −108.35 (2F:=CHCF$_2$—), −109.81 (1F:=CF—), −112.34 (2F:—CF$_2$CH=), −117.4 to 126.3 (10F:—CF$_2$—)

Example 2

In Example 1, the amount of DBU used was changed to 1.3 g (8.5 mmol), and then the reaction was carried out, thereby obtaining 1.2 g (yield: 33%) of mixture of products A and B (weight ratio: 48:52), which was the above fraction, and 0.6 g (purity: 98%, yield: 15%) of the following product C, which was a fraction with a vapor temperature of 76 to 77° C./1 kPa.
Product C: 3,3,4,4,5,5,6,6,7,7,9,9,10,10,11,11,12,12,12-nonadecafluoro-1-dodecene
$CF_3CF_2CF_2CF_2CH_2CF_2CF_2CF_2CF_2CF_2CH=CH_2$
$^{1}H$-NMR δ=2.90 (2H:—CH$_2$—), 5.79 (1H:—CF$_2$—CH=), 5.97 (2H:=CH$_2$)
$^{19}F$-NMR δ=−82.02 (3F:CF$_3$—), −113.04 (4F:—CF$_2$CH$_2$—), −114.79 (2F:—CF$_2$CH=), −121.9 to −128.2 (10F:—CF$_2$—)

Example 3

In Example 1, 1.8 g (17.3 mmol) of triethylamine was used in place of DBU, and the total reaction time was changed to 48 hours. Then, the reaction was carried out, thereby obtaining 2.0 g (yield: 55%) of mixture of products A and B (weight ratio: 49:51), which was the above fraction, and 1.0 g (yield: 26%) of product C, which was the above fraction.

Example 4

In Example 3, 15 ml of tetrahydrofuran was used as a solvent in place of the fluorine-containing organic solvent, the reaction temperature was changed to 50° C., and the total reaction time was changed to 24 hours. Then, the reaction was carried out, thereby obtaining 2.7g (yield: 74%) of mixture of products A and B (weight ratio: 49:51), which was the above fraction.

Reference Example 2

A compound of the formula: $CF_3(CF_2)_3(CH_2CF_2)(CF_2CF_2)I$ (99 GC %) (509 g; 0.99 mol) and 6.7 g (0.05 mol) of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 38 g (1.35 mol) of ethylene was introduced over about 3 hours. The content was collected at an internal temperature of 50° C. or less, thereby obtaining 530 g (yield: 96%) of a compound of the formula: $CF_3(CF_2)_3(CH_2CF_2)(CF_2CF_2)(CH_2CH_2)I$ (98 GC %), i.e., the formula: $C_4F_9CH_2(CF_2)_3CH_2CH_2I$.

Example 5

3,3,4,4,5,5,7,7,8,8,9,9,10,10,10-pentadecafluoro-1-iodododecane of the formula: $C_4F_9CH_2(CF_2)_3CH_2CH_2I$ (5 g; 9.3 mmol) obtained in above Reference Example 2 was dissolved in 15 ml of fluorine-containing organic solvent (AK-225; a product of Asahi Glass), and the resulting solution was placed in a 50-ml glass reactor equipped with a cooling condenser, thermocouple, and magnet stirrer. After ice cooling, 3.0 g (19.7 mmol) of 1,8-diazabicyclo[5.4.0]-7-undecene [DBU] was added dropwise while maintaining the internal temperature in a range of 0 to 10° C. After completion of the addition, the mixture was stirred at about 0° C. for about 1 hour, and stirring was then continued at room temperature for about 23 hours (total reaction time: 24 hours).

After the reaction was completed, washing with 20 ml of water was performed twice, and subsequently washing with a saturated saline solution was performed once. The obtained reaction solution was dehydrated and dried over anhydrous magnesium sulfate. After the reaction solvent was distilled off under reduced pressure, the residue was purified by distillation under reduced pressure, thereby obtaining 2.5 g (yield: 66%) of a fraction with a vapor temperature of 53 to 55° C./1 kPa. The structure of the obtained fraction was determined by $^{19}$F-NMR and $^{1}$H-NMR, and the fraction was identified as a mixture of products D and E having a weight ratio of about 47:53.

Product D: 3,3,4,4,5,5,7,8,8,9,9,10,10,10-tetradecafluorodeca-1,6-diene
$CF_3CF_2CF_2CF=CHCF_2CF_2CF_2CH=CH_2$ Product E: 3,3,4,4,5,7,7,8,8,9,9,10,10,10-tetradecafluorodeca-1,5-diene
$CF_3CF_2CF_2CF_2CH=CFCF_2CF_2CH=CH_2$ $^{1}$H-NMR: TMS
Product D δ=5.81 (1H:—CH=CF—), 5.79 (1H:—CF$_2$—CH=), 5.97 (2H:=CH$_2$)
Product E δ=5.82 (1H:—CH=CF—), 5.79 (1H:—CF$_2$—CH=), 5.97 (2H:=CH$_2$)

$^{19}$F-NMR: CFCl$_3$
Product D δ=−80.23 (3F:CF$_3$—), −107.80 (2F:=CHCF$_2$—), −111.34 (1F:–CF=), −112.42 (2F:—CF$_2$CH=), −116.7 to 128.2 (6F:—CF$_2$—)
Product E δ=−79.97 (3F:CF$_3$—), −108.35 (2F:=CHCF$_2$—), −111.34 (1F:=CF—), −112.42 (2F:—CF$_2$CH=), −116.7 to 128.2 (6F:—CF$_2$—)

Example 6

(1) A 30-L stainless steel reactor equipped with a stirrer was vacuumized, and the following components were placed therein:

| Water | 13 kg |
| C$_7$F$_{15}$COONH$_4$ | 39 g |
| Na$_2$HPO$_4$•12H$_2$O | 26 g |
| CBr$_2$=CHF | 26 g |
| ICF$_2$CF$_2$Br | 24 g |
| Diene mixture obtained in Example 5 | 45 g |

C$_3$F$_7$CF=CHCF$_2$CF$_2$CF$_2$CH=CH$_2$ (47 mol %)
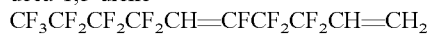
C$_4$F$_9$CH=CFCF$_2$CF$_2$CH=CH$_2$ (53 mol %)

Thereafter, 490 g (13 mol %) of tetrafluoroethylene [TFE], 1180 g (47 mol %) of vinylidene fluoride [VdF], and 2330 g (40 mol %) of hexafluoropropylene [HFP] were added thereto, and the temperature was increased to 70° C. The pressure after the temperature increase was 3.88 MPa·G. The diene mixture was added in a total of 20 batches at the beginning of the polymerization reaction and during the divided addition of mixed gas.

Subsequently, a polymerization initiator aqueous solution, in which 24 g of ammonium persulfate was dissolved in 500 g of water, was press-charged into the reactor to initiate the polymerization reaction. Since the pressure in the reactor decreased along with the progress of the polymerization reaction, a TFE/VdF/HFP (mol % 16.4/62.2/21.4) mixed gas was added to the reactor in batches to maintain the pressure at 3.75 to 3.85 MPa·G. The addition was stopped when the total amount of mixed gas added was 10.2 kg (about 10 hours after the start of the reaction), and aging was performed for about 30 to 50 minutes. The pressure in the reactor at this time was 1.8 MPa·G.

After the reaction was, completed, the reaction mixture was taken out of the reactor and coagulated with an aqueous calcium chloride solution, thereby obtaining a fluorine-containing elastomer A. The NMR analysis of copolymerization composition of the obtained fluorine-containing elastomer A revealed that the elastomer was a VdF/TFE/HFP (mol % 67.1/16.0/16.9) copolymer.

(2) The fluorine-containing elastomer A (100 parts by weight) obtained above, 20 parts by weight of MT carbon black, 5 parts by weight of zinc oxide, 5 parts by weight of triallyl isocyanurate (TAIC M60; a product of Nippon Kasei Chemical Co., Ltd.), and 3.5 parts by weight of organic peroxide (Perhexa 25B40; a product NOF Corporation) were kneaded by an open roll. The mixture was subjected to press vulcanization at 180° C. for 10 minutes, followed by oven vulcanization (secondary vulcanization) at 230° C. for 22 hours. The resulting vulcanizate was measured for hardness (according to JIS K6253, which corresponds to ISO 48), tensile properties (according to JIS K6251, which corresponds to ISO 37), and compression set (ASTM Method-B/P-24 O ring; 200° C., 70 hours).

Example 7

(1) A 30-L stainless steel reactor equipped with a stirrer was vacuumized, and the following components were placed therein:

| Water | 15.5 kg |
| C$_7$F$_{15}$COONH$_4$ | 71 g |
| Na$_2$HPO$_4$•12H$_2$O | 51 g |
| ICF$_2$CF$_2$CF$_2$I | 45 g |
| Diene mixture obtained in Example 5 | 45 g |

C$_3$F$_7$CF=CHCF$_2$CF$_2$CF$_2$CH=CH$_2$ (47 mol %)
C$_4$F$_9$CH=CFCF$_2$CF$_2$CH=CH$_2$ (53 mol %)

Thereafter, 210 g (8 mol %) of tetrafluoroethylene [TFE], 1140 g (70 mol %) of vinylidene fluoride [VdF], and 930 g (22 mol %) of perfluoro(methyl vinyl ether) [FMVE] were added thereto, and the temperature was increased to 80° C. The pressure after the temperature increase was 3.11 MPa·G. The diene mixture was added in a total of 20 batches at the beginning of the polymerization reaction and during the divided addition of mixed gas.

Subsequently, a polymerization initiator aqueous solution, in which 0.8 g of ammonium persulfate was dissolved in 500 g of water, was press-charged into the reactor to initiate the polymerization reaction. Since the pressure in the reactor decreased along with the progress of the polymerization reaction, a TFE/VdF/FMVE (mol % 9.0/73.0/18.0) mixed gas was added to the reactor in batches to maintain the pressure at 2.9 to 3.0 MPa·G. The addition was stopped when the total amount of mixed gas added was 7.2 kg (about 4 hours after the start of the reaction), and aging was performed for about 120 minutes. The pressure in the reactor at this time was 1.2 MPa·G.

After the reaction was completed, the reaction mixture was taken out of the reactor and coagulated with an aqueous calcium chloride solution, thereby obtaining a fluorine-containing elastomer B. The NMR analysis of copolymerization composition of the obtained fluorine-containing elastomer B revealed that the elastomer was a VdF/TFE/FMVE (mol % 72.8/9.0/18.2) copolymer.

(2) The fluorine-containing elastomer B (100 parts by weight) obtained above, 30 parts by weight of MT carbon black, 6 parts by weight of zinc oxide, 6.7 parts by weight of triallyl isocyanurate (TAIC M60; a product of Nippon Kasei Chemical Co., Ltd.), and 1.3 parts by weight of organic peroxide (Perhexa 25B40; a product of NOF Corporation) were kneaded by an open roll. The mixture was subjected to press vulcanization at 180° C. for 10 minutes, followed by oven vulcanization (secondary vulcanization) at 220° C. for 22 hours. The resulting vulcanizate was measured for hardness, tensile properties, and compression set.

Comparative Example 1

In Example 6, no diene mixture was used in the copolymerization reaction. Polymerization composition of the obtained fluorine-containing elastomer C was a VdF/TFE/HFP (mol % 67.0/16.0/17.0) copolymer. The vulcanization using the fluorine-containing elastomer C was also carried out in the same manner as in Examiner 6.

Comparative Example 2

In Example 7, 34 g of a compound of the formula: $CF_2=CFOCF_2CF_2OCF=CF_2$ was used in place of the diene mixture. Polymerization composition of the obtained fluorine-containing elastomer D was a VdF/TFE/FMVE (mol % 73.2/9.0/17.8) copolymer. The vulcanization using the fluorine-containing elastomer D was also carried out in the same manner as in Example 7.

Comparative Example 3

In Example 7, no diene mixture was used in the copolymerization reaction. Polymerization composition of the obtained fluorine-containing elastomer E was a VdF/TFE/FMVE (mol % 73.0/9.0/18.0) copolymer. The vulcanization using the fluorine-containing elastomer E was also carried out in the same manner as in Example 7.

The following Table shows the measurement results of Examples 6 and 7, and Comparative Example 1 to 3.

TABLE

| Measurement item | Ex. 6 | Ex. 7 | Comp. Ex. 1 | Comp. Ex. 2 | Comp. Ex. 3 |
|---|---|---|---|---|---|
| Hardness (Duro A) | 70 | 71 | 68 | 70 | 70 |
| 100% modulus (MPa) | 4.9 | 5.1 | 4.2 | 5.2 | 4.6 |
| Strength at break (MPa) | 22.6 | 23.1 | 22.2 | 20.2 | 21.0 |
| Elongation at break (%) | 320 | 300 | 310 | 220 | 280 |
| Compression set (%) | 33 | 20 | 39 | 21 | 27 |

The invention claimed is:

1. A mixture of polyfluoroalkadienes represented by the general formulae:

$$CF_3(CF_2)_nCF=CH(CF_2)_{m+1}CH=CH_2 \quad [Ia]$$

and $$CF_3(CF_2)_{n+1}CH=CF(CF_2)_mCH=CH_2 \quad [Ib]$$

wherein n is an integer of 0 to 5, and m is an integer of 0 to 6.

2. A method of producing the polyfluoroalkadiene mixture of claim 1 as a mixture fraction of products [Ia] and [Ib], the method comprising reacting a perfluoroalkyl iodide represented by the general formula:

$$CF_3(CF_2)_{n+1}CH_2(CF_2)_{m+1}(CH_2CH_2)I \quad [II]$$

wherein n is an integer of 0 to 5, and m is an integer of 0 to 6, with an organic basic compound.

3. The method of producing the polyfluoroalkadiene mixture according to claim 2, wherein the organic basic compound is used in a molar ratio of 1.95 to 2.5 with respect to the polyfluoroalkyl iodide.

4. The method of producing the polyfluoroalkadiene mixture according to claim 2, wherein the organic basic compound is a nitrogen-containing organic basic compound.

5. The method of producing the polyfluoroalkadiene mixture according to claim 4, wherein the nitrogen-containing organic basic compound is 1,8-diazabicyclo[5.4.0]-7-undecene.

6. The method of producing the polyfluoroalkadiene mixture according to claim 4, wherein the reaction is carried out in a fluorine-containing organic solvent.

7. The method of producing the polyfluoroalkadiene mixture according to claim 4, wherein the nitrogen-containing organic basis compound is triethylamine.

8. The method of producing the polyfluoroalkadiene mixture according to claim 7, wherein the reaction is carried out in a tetrahydrofuran solvent.

9. The polyfluoroalkadiene mixture according to claim 1, which is used as a copolymerizable monomer of a fluorine-containing elastomer.

10. A peroxide-crosslinkable fluorine-containing elastomer, which is a fluorine-containing copolymer obtained by copolymerizing the polyfluroalkadiene mixture of claim 9 as a copolymerizable monomer, with a fluorinated olefin monomer.

11. The peroxide-crosslinkable fluorine-containing elastomer according to claim 10, wherein the fluorine-containing copolymer copolymerized with the polyfluoroalkadiene mixture is a vinylidene fluoride-tetrafluoroethylene-based copolymer.

12. The peroxide-crosslinkable fluorine-containing elastomer according to claim 11, wherein the vinylidene fluoride-tetrafluoroethylene-based copolymer is a vinylidene fluoride-tetrafluoroethylene-hexafluoropropylene copolymer or a vinylidene fluoride-tetrafluoroethylene-perfluoro(lower alkyl vinyl ether) copolymer.

* * * * *